(12) United States Patent
Yang et al.

(10) Patent No.: US 11,227,671 B2
(45) Date of Patent: Jan. 18, 2022

(54) METHODS AND APPARATUS FOR DOUBLE-INTEGRATION ORTHOGONAL SPACE TEMPERING

(71) Applicant: The Florida State University Research Foundation, Inc., Tallahassee, FL (US)

(72) Inventors: Wei Yang, Tallahassee, FL (US); Lianqing Zheng, Tallahassee, FL (US)

(73) Assignee: The Florida State University Research Foundation, Inc., Tallahassee, FL (US)

(*) Notice: Subject to any disclaimer, the term of this patent is extended or adjusted under 35 U.S.C. 154(b) by 918 days.

(21) Appl. No.: 15/981,528

(22) Filed: May 16, 2018

(65) Prior Publication Data

US 2018/0285534 A1    Oct. 4, 2018

Related U.S. Application Data

(63) Continuation-in-part of application No. 14/104,375, filed on Dec. 12, 2013, now abandoned, which is a continuation-in-part of application No. PCT/US2012/042405, filed on Jun. 14, 2012.

(60) Provisional application No. 61/496,628, filed on Jun. 14, 2011.

(51) Int. Cl.
*G16C 10/00* (2019.01)
*G16B 5/00* (2019.01)
*G16C 20/50* (2019.01)
*G16C 20/90* (2019.01)
*G16B 5/30* (2019.01)

(52) U.S. Cl.
CPC ............... *G16C 10/00* (2019.02); *G16B 5/00* (2019.02); *G16B 5/30* (2019.02); *G16C 20/50* (2019.02); *G16C 20/90* (2019.02)

(58) Field of Classification Search
None
See application file for complete search history.

*Primary Examiner* — Soren Harward
(74) *Attorney, Agent, or Firm* — Eversheds Sutherland (US) LLP

(57) ABSTRACT

The orthogonal space random walk (OSRW) algorithm is generalized to be the orthogonal space tempering (OST) method via the introduction of the orthogonal space sampling temperature. Moreover, a double-integration recursion method is developed to enable practically efficient and robust OST free energy calculations, and the algorithm is augmented by a novel θ-dynamics approach to realize both the uniform sampling of order parameter spaces and rigorous end point constraints. In the present work, the double-integration OST method is employed to perform alchemical free energy simulations, specifically to calculate the free energy difference between benzyl phosphonate and difluorobenzyl phosphonate in aqueous solution, to estimate the solvation free energy of the octanol molecule, and to predict the nontrivial Barnase-Barstar binding affinity change induced by the Barnase N58A mutation. As demonstrated in these model studies, the DI-OST method can robustly enable practically efficient free energy predictions, particularly when strongly coupled slow environmental transitions are involved.

14 Claims, 2 Drawing Sheets

METHODS AND APPARATUS FOR DOUBLE-INTEGRATION ORTHOGONAL SPACE TEMPERING

CROSS-REFERENCE TO RELATED APPLICATIONS

This application is a continuation-in-part of U.S. patent application Ser. No. 14/104,375, filed on Dec. 12, 2013, which claims is a continuation-in-part of PCT/US2012/042405, filed on Jun. 14, 2012 which claims the benefit of U.S. Provisional Patent Application No. 61/496,628, filed Jun. 14, 2011, all of which are incorporated by reference herein and which forms a part of the disclosure in this application.

STATEMENT OF GOVERNMENT INTEREST

This invention was made with U.S. Government support under MCB Grant No. 0919983 awarded by the National Science Foundation. The U.S. Government has certain rights in this invention.

FIELD OF THE INVENTION

This invention relates broadly to mathematical simulations in molecular biology. More particularly, this invention relates to methods for calculating alchemic free energies to predict the free energy difference between benzyl phosphonate and difluorobenzyl phosphonate in aqueous solution, to estimate the $pK_a$ value of a buried titratable residue, Glu-66, in the interior of the V66E staphylococcal nuclease mutant, and to predict the binding affinity of xylene in the $T_4$ lysozyme $L_{99}A$ mutant.

BACKGROUND

On average it takes 12-15 years and $800 million for a safe and effective new drug to go from a discovery in the lab to the pharmacy. If the costs of drugs which fail partway through the process are accounted for, the price rises to $1.3 billion—for a single drug.

Despite progress made over the past two decades, computational predictions for docking and scoring (molecules and proteins) have yet to meet the necessary level of consistency and accuracy. One recent study of binding affinity predictions states, "Accurate ligand-protein binding affinity prediction, for a set of similar binders, is a major challenge in the lead optimization stage in drug development. In general, docking and scoring functions perform unsatisfactorily in this application.

Of the approximately 5,000 compounds that enter the medicinal chemistry and drug metabolism and pharmacokinetics evaluation phases of drug discovery, only one succeeds and becomes a drug. If prioritization and screening occurred more rapidly, pharmaceutical companies could bring drugs to market more quickly and earn revenue on patented products for more years than with the current technologies.

A drug is generally a small molecule that activates or inhibits the function of a protein or receptor, which in turn results in a therapeutic benefit to a patient. In the most basic sense, drug design involves the design of small molecules that are complementary in shape and charge to the biomolecular target with which they interact and bind. Drug design frequently relies on computer modeling techniques. This type of modeling is often referred to as Computer Aided Drug Design (CADD). Finally, drug design that relies on the knowledge of the three-dimensional structure of the biomolecular target is known as Structure Based Drug Design.

What is really meant by drug design is ligand design, that is, the design of a (small) molecule that will bind tightly to its target. Although modeling techniques for prediction of binding affinity are reasonably successful, there are many other properties, such as bioavailability, metabolic half-life, and lack of side effects, that must be optimized before a ligand can become a safe and efficacious drug.

Structure Based Drug Design is a powerful method for rapidly identifying new lead compounds when a receptor (target) structure is available. In the early stages of drug discovery, virtual high throughput screening (VHTS) can lead to increased efficiency by helping to prioritize compounds in a library and by reducing library size. During the lead optimization stage, accurate docking methods, efficient de novo design methods, and accurate physics-based scoring can yield high-confidence compounds that are more likely to be active in vivo. There are several areas where molecular modeling may prove helpful.

Virtual Screening: In Virtual Screening, a large chemical panel is screened against a protein to shortlist those molecules, which may have better binding affinity for the protein. If there is a "hit" with a particular compound, it can be extracted for further in-silico testing and then taken into the laboratory for physical validation. With today's computational resources, several million compounds can be screened in a few days on large clustered computers. Pursuing a handful of promising leads for further development can save researchers considerable time and expense.

Homology Modeling: Another common challenge in computer aided drug design research is determining the 3-D structure of proteins. The 3-D structure is known for only a small fraction of proteins. Homology modeling is one method used to predict the protein 3-D structure. If the structure of a specific protein (target) is not known, then it is modeled, based on the known 3-D structures of other similar proteins (templates) using the homology modeling technique.

Quantitative structure activity relationship (QSAR): QSAR is the process by which chemical structures are quantitatively correlated for their biological activity or chemical reactivity, based on well-defined statistical modeling process. The correlations and the statistical models are then used to predict the biological response of the other chemically similar structures.

Drug lead optimization: When a promising lead candidate has been found in a drug discovery program, the next step is to optimize the structure and properties of the potential drug. This usually involves a series of modifications to the primary structure (scaffold) of the compound. This process can be enhanced using software tools that explore related compounds with respect to the lead candidate.

Similarity searches: A common activity in drug discovery is the search for similar chemical compounds. There are variety of methods used in these searches, including sequence similarity, 2D and 3D shape similarity, substructure similarity, electrostatic similarity and others. Several chemo-informatics tools and search engines are available for this work.

Pharmacophore modeling: Pharmacophore is defined as the three-dimensional arrangement of atoms, or groups of atoms, responsible for the biological activity of a drug molecule. Pharmacophore models are constructed, based on compounds of known biological activity and are refined as more data are acquired in an iterative process. The models can be used for optimizing a series of known ligands or, alternatively, they can be used to search molecular databases in order to find new structural classes.

Drug bioavailability and bioactivity: Many drug candidates fail in Phase III clinical trials after many years of research and millions of dollars have been spent on them. And most fail because of toxicity or problems with metabolism. The key characteristics for drugs are absorption, distribution, metabolism, excretion, toxicity and efficacy, i.e. bioavailability and bioactivity. Although, these properties are usually measured in the lab, they can also be predicted in advance with bioinformatics software.

In rational design, docking—the process of positioning a ligand molecule or protein in a receptor binding sites—and scoring—the assessment of the fitness of docked ligands—are used to predict binding configuration of active ligands, screen a library of small molecules, and estimate the binding affinities of a compound site. Correct binding configuration offers tremendous insights into the key interaction between ligand and protein molecules and is extremely valuable for understanding the molecular structure activity relationship and for guiding the optimization of the lead compounds.

Despite the progress made over the past two decades, computational predictions for docking and scoring have not yet met the expectation of consistency and accuracy across a wide range of systems. Recent studies have shown that none of the existing docking programs are able to predict experimental binding poses consistently for diverse protein-ligand complexes. Moreover, ranking a series of ligand molecules/proteins is a far more difficult challenge.

There are two major technical obstacles: 1. Reliability of conformational sampling of the complex between ligand (drug or protein) and protein, and 2. Accuracy of predicated binding free energy changes upon the modifications of ligands.

One of key reasons for the modest success using traditional docking methods in predicting the binding affinity is that they are based on ad-hoc sampling and empirical scoring function, which sacrifices prediction reliability for high computational efficiency. The state-of-the-art of computer-aided design methods remain at the qualitative level. As is generally observed, quantitative prediction of relative binding affinities is still not routinely achievable; and even when it is occasionally realized, great "expert insights" and/or large computing resources are usually required. Therefore, pharmaceutical companies are desperate for a quantitative tool, which can reliably predict binding affinity changes upon chemical or biochemical modifications, so as to further improve their interests in potential drug candidate in terms of time, labor, and research cost.

The pharmaceutical ranking of ligand docking molecules historically is a capital intensive billion dollar step in the discovery of clinically relevant drugs. There are many open source software programs and a few commercial software programs for ligand binding prediction. They are based on five underlying approaches: free energy perturbation (FEP), Classical FEP, Monte Carlo, Linear Interaction Energy (LIE) and end-point free energy methods (MM/PBSA).

State of the art computer aided drug design relies on clusters of CPUs and simulation times are on the order of weeks to months. Clearly, the unmet need for the pharmaceutical companies is a software/hardware product that will screen dozens or hundreds of ligands in days with little technical input and a consistent, reliable output that is quantitative and not just qualitative.

The inventors' earlier work is well explained in "Random Walk in Orthogonal Space to Achieve Efficient Free-Energy Simulation Of Complex Systems", www.pnas.org/cgi/doi/10.1073/pnas.0810631106; PNAS (Proceedings of the National Academy of Sciences of the United States of America) Dec. 23, 2008, vol. 105, no. 51, 20227-20232 which is incorporated by reference herein.

In the past few decades, many ingenious efforts have been made in the development of free-energy simulation methods. Because complex systems often undergo nontrivial structural transition during state switching, achieving efficient free-energy calculation can be challenging. As identified in the prior art, the "Hamiltonian" lagging, which shows that necessary structural relaxation falls behind the order parameter move, has been a primary problem for achieving efficiency in free-energy simulation.

Developing free energy calculation methods has been a focal area in the quantitative aspect of molecular simulation. A major goal is to achieve accurate estimation of target free energy changes within as short as possible sampling length. Facing the bottleneck sampling challenge, various methods have been proposed; among many ingenious efforts, generalized ensemble (GE) based algorithms have attracted tremendous attention. The essential idea of GE free energy simulation methods is to employ a modified ensemble, which permits quick escaping of local energy wells, to efficiently produce accurate distributions for free energy estimations. In classical GE (or the first-order GE) free energy simulations, the design of a modified ensemble is focused on a prechosen order parameter $\lambda$, as reflected by the biasing energy term $f_m(\lambda)$ in the following target potential shown in Equation (1).

$$U_m = U_O(\lambda) + f_m(\lambda) \quad (1)$$

When $\lambda$ is a spatial order parameter, $U_O(\lambda)$ represents the target energy function; when $\lambda$ is an alchemical order parameter, $U_O(\lambda)$ stands for a hybrid energy function that is constructed on the basis of the constraints of $U_O(0)=UA$ and $U_O(1)=UB$ (then, two end states A and B are respectively represented by $\lambda=0$ and $\lambda=1$). In the first-order GE regime, the biasing term $f_m(\lambda)$ is adaptively updated to approach $-G_O(\lambda)$, which is the negative of the $\lambda$-dependent free energy profile corresponding to the canonical ensemble with $U_O(\lambda)$ as the potential energy function; thereby, an order parameter space random walk can be achieved to uniformly sample all the states in a target range. To adaptively estimate $G_O(\lambda)$, three major recursion approaches have been developed, they include the adaptive umbrella sampling method in which free energy estimations are based on order parameter probability distributions, the adaptive biasing force (ABF) method (in alchemical free energy simulations, it is called the generalized ensemble thermodynamic integration method in the molecular dynamics scheme, or the adaptive integration method in the Monte Carlo or hybrid Monte Carlo scheme), in which free energy estimations are based on the thermodynamic integration (TI) formula and the multiplicative approaches (including the metadynamics method for molecular dynamics simulations and the Wang-Landau method for Monte Carlo or hybrid Monte Carlo simulations), which are realized through a dynamic force-balancing relationship. It is noted that various hybrid recursion methods based on the above three major approaches have been explored as well.

Although in first-order GE simulations, free energy surfaces along pre-chosen order parameters are flattened, "hidden" free energy barriers usually exist in the space perpendicular to the order parameter directions. Notably, these "hidden" free energy barriers can impose great sampling challenges, e.g., slow environmental relaxations. As discussed in our earlier works, the generalized force $F\lambda$ can serve as a collective variable to describe the progress of the hidden processes that strongly couple with the order parameter move. It is noted that $F\lambda$ is defined as $\partial U_O/\partial \lambda -RT(\partial \ln|J|/\partial \lambda)$, where $|J|$ is the Jacobian term corresponding to the transformation from the Cartesian system to a new system with $\lambda$ as a coordinate direction, and it is equal to $\partial U_O/\partial x$ in this model case because of the fact that here an original Cartesian coordinate x is employed as the order parameter. The above insight was originally derived from the Marcus theory and in our earlier work we generalized the vertical energy gap which was to describe electron transfer processes, to be the generalized force for the description of transitions between neighboring order parameter states, it can be clearly revealed by the spatial-dependent $\partial U_0/\partial x$ function. Near the state transition region [$x \in (-0.5,0.5)$], $\partial U_0/\partial x$ decreases monotonically with the increase of y. Accordingly, the second-order GE simulation scheme, originally the orthogonal space random walk (OSRW) algorithm, was formulated as shown in the following modified energy function of Equation (2).

$$U_m = U_0(\lambda) + f_m(\lambda) + g_m(\lambda, F_\lambda) \quad (2)$$

where $f_m(\lambda)$ is targeted toward $-G_0(\lambda)$, and $g_m(\lambda, F_\lambda)$ is targeted toward $-G_0(\lambda, F_\lambda)$, the negative of the free energy profile along $(\lambda, F_\lambda)$ in the ensemble corresponding to the energy function $U_0(\lambda) - G_0(\lambda)$. It is noted that, different from the first-order GE methods, OSRW requires two recursion components to respectively update $g_m(\lambda, F_\lambda)$ and $f_m(\lambda)$. The recursion component responsible for the update of $g_m(\lambda, F_\lambda)$ is called the "recursion kernel", and the recursion component responsible for the update of $f_m(\lambda)$ is called the "recursion slave" because of the fact that the target of $f_m(\lambda)$, $-Go(\lambda)$, depends on the target of $g_m(\lambda, F_\lambda)$: $-G_0(\lambda, F_\lambda)$. In the original development, the recursion slave was based on the TI formula, and the metadynamics method was employed as the recursion kernel. Notably, in practice, the recursion kernel can be based on any of the three recursion methods as previously mentioned.

Since its birth, the OSRW method has shown very encouraging sampling power, however, the originally implemented method suffers from the lack of robustness, especially in the aspect of long-time scale convergence. Two inter-related aspects contribute to this robustness issue: (1) because of the fact that free energy surfaces along generalized force directions are completely flattened (e.g., the effective sampling temperature in the orthogonal space is infinity), there is no boundary to confine the orthogonal space sampling exploration; (2) the metadynamics-based recursion kernel needs to be replaced by a new more robust recursion strategy.

In our previous work, we proposed a method using a random walk in both the order parameter space and its generalized force space, thereby, the order parameter move and the required conformational relaxation could be efficiently synchronized. As demonstrated in both the alchemical transition and the conformational transition, a leapfrog improvement in free-energy simulation efficiency was obtained. In particular, (i) it solved the notoriously challenging problem of accurately predicting the $pK_a$ value of a buried titratable residue, Asp-66, in the interior of the V66E staphylococcal nuclease mutant, and (ii) it achieved superior efficiency over the prior metadynamics methods. However, the orthogonal space random walk method proposed in our previous work was not robust enough for practical use.

SUMMARY OF THE INVENTION

The present invention provides an orthogonal space tempering method which provides robust simulation predictions. The invention also provides a novel recursion kernel which provides much more efficient simulation predictions.

The orthogonal space tempering technique is provided via the introduction of an orthogonal space sampling temperature. Moreover, based on a "dynamic reference restraining" strategy, a novel double-integration recursion method is provided as the recursion kernel to enable practically efficient and robust orthogonal space tempering free energy calculations. The provided double-integration orthogonal space tempering method is demonstrated on alchemical free energy simulations, specifically to calculate the free energy difference between benzyl phosphonate and difluorobenzyl phosphonate in aqueous solution, to estimate the $pK_a$ value of a buried titratable residue, Glu-66, in the interior of the V66E staphylococcal nuclease mutant, and to predict the binding affinity of xylene in the $T_4$ lysozyme $L_{99}A$ mutant. The double integration orthogonal space tempering method according to the invention provides unprecedented efficiency and robustness.

The present invention is focused on alchemical free energy simulations by which protein-ligand binding, protein-protein binding, solvation energies, pKa values, and other chemical state related thermodynamic properties can be predicted. However, the double integration orthogonal space tempering method according to the invention is also applicable to geometry-based potential of mean force calculations. The present invention is at least partially described in "Practically Efficient and Robust Free Energy Calculations: Double-Integration Orthogonal Space Tempering", http://pubs.acs.org/doi/abs/10.1021/ct200726v, J. Chem. Theory Comput. 2012, 8, 810-823, published Jan. 25, 2012.

Regarding the first aspect, here, we are proposing to generalize the OSRW method to the orthogonal space tempering (OST) technique, which can be described through the following modified energy function shown in Equation (3).

$$U_m = U_o(\lambda) + f_m(\lambda) + \frac{T_{ES} - T_O}{T_{ES}} g_m(\lambda, F_\lambda) \quad (3)$$

where $g_m(\lambda, F_\lambda)$ is still targeted toward $-G_O(\lambda, F_\lambda)$; its contribution to the overall potential is scaled by a parameter of $(T_{ES}-T_O)/T_{ES}$; here $T_O$ is the system reservoir temperature, and a preset parameter $T_{ES}$ can be called the orthogonal space sampling temperature because of the fact that for any given $\lambda'$ state, probability distributions in the target ensemble follow $\exp[-G_O(\lambda',F_\lambda)/kT_{ES}]$, where k is the Boltzmann constant. Thereby, the sampling boundary in the orthogonal space is naturally defined. In regard to the second aspect, the long-time convergence of the ABF recursion strategy has been mathematically proven, therefore, we will employ this recursion approach as a key component of our recursion kernel design to ensure overall free energy recursion robustness.

In the present invention, the double-integration OST (DI-OST) method is described in the context of alchemical free energy simulation (or called the "free energy perturbation" calculation); for the purpose of GE sampling, the dynamics of the scaling parameter $\lambda$ are introduced via a specially designed extended Hamiltonian scheme. The present double-integration OST (DI-OST) method is demonstrated on alchemical free energy simulations, specifically to calculate the free energy difference between benzyl phosphonate and difluorobenzyl phosphonate in aqueous solution, to estimate the solvation free energy of the octanol molecule, and to predict the nontrivial Barnase-Barstar binding affinity change induced by the Barnase N58A mutation. As shown in these model studies, the DI-OST method is a practically efficient and robust free energy calculation method, particularly when strongly coupled slow environmental transitions are involved.

Additional objects and advantages of the invention will become apparent to those skilled in the art upon reference to the detailed description taken in conjunction with the provided figures.

DETAILED DESCRIPTION

Figure 1:
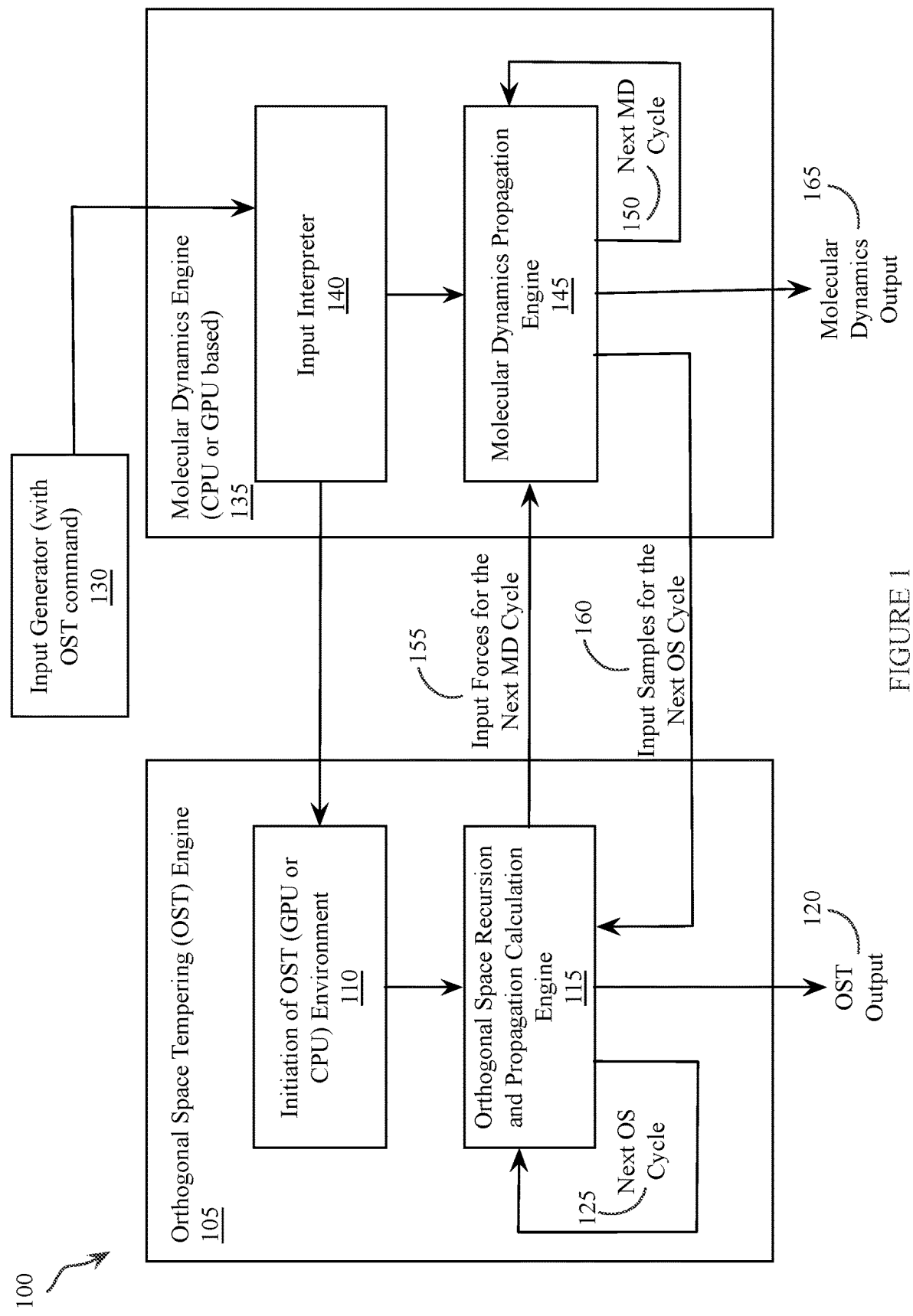
FIG. 1 is a high level block diagram illustrating an apparatus and data flow in accordance with an embodiment of the present invention.

The present invention is focused on alchemical free energy simulations, by which protein-ligand binding affinity changes, protein-protein binding affinity changes, solvation energies, $pK_a$ values, and other chemical state related thermodynamic properties can be predicted. The disclosed DI-OST algorithm is also applicable to the geometry-based potential of mean force calculations.

To carry out alchemical free energy calculations, as described in Equation (1), a scaling parameter $\lambda$ needs to be introduced to connect two target chemical states. A simplest hybrid energy function is the linear form shown in Equation (4).

$$U_O(\lambda) = (1-\lambda)U_S^A + \lambda U_S^B + U_e \tag{4}$$

where $U_S^A$ and $U_S^B$ are the energy terms unique in the two end chemical states; $U_e$ represents the common environment energy terms shared by the two end states. When dummy atoms are employed in one of the end states, soft-cores potentials are commonly applied to treat the van der Walls terms or/and the electrostatic terms in $U_S^A$ and $U_S^B$ to avoid the end point singularity issue.

In GE alchemical free energy simulations, $\lambda$ needs to be dynamically coupled with the motion of the rest of the system. Such extended dynamics can be realized either via the hybrid Monte Carlo method, where the scaling parameter jumps along a prearranged discrete $\lambda$ ladder are enabled through the metropolis acceptance/rejection procedure, or via the $\lambda$-dynamics method, where $\lambda$ moves in the continuous region between 0 and 1 are enabled through an extended Hamiltonian approach. The extended dynamics of the scaling parameter in OSRW are implemented on the basis of the $\lambda$-dynamics method. In the original $\lambda$-dynamics free energy calculation method, the scaling parameter $\lambda$ is treated as a one-dimensional fictitious particle. In the present invention, especially to rigorously constrain $\lambda$ between 0 and 1, a novel $\theta$-dynamics approach is proposed. In this $\theta$-dynamics, $\lambda$ is set as the function $\lambda(\theta)$, the variable $\theta$ is treated as a one-dimensional fictitious particle, which travels periodically between $-\pi$ and $\pi$. In OSRW simulations, uniform distributions are targeted. Here, the usage of the $\theta$-dynamics approach is mainly for the purpose of constraining the $\lambda$ range. Actually, it is preferable to have uniform sampling in the $\lambda$ space. For the above purpose, the functional form of $\lambda(\theta)$ according to the design is as shown in Equation (5).

$$\lambda(\theta) = \begin{cases} r\sin^2\frac{\theta}{2}, |\theta| \le \theta_o \\ a\theta + b, \theta_o < \theta < \pi - \theta_o \\ -a\theta + b, \theta_o - \pi < \theta < -\theta_o \\ r\sin^2\frac{\theta}{2} + c, \pi - \theta_o \le |\theta| \le \pi \end{cases} \tag{5}$$

in which $r = 1/(1-\cos\theta_O + \frac{1}{2}(\pi - 2\theta_O)\sin\theta_O)$, $a = r/2\sin\theta_O$, $b = r/2(1-\cos\theta_O - \theta_O\sin\theta_O)$, and $c = r/2(\pi - \theta_O)\sin\theta_O + r/2(1-\cos\theta_O - \theta_O\sin\theta_O) - r\sin^2((\pi-\theta_O)/2)$. In Equation (5), $\theta_O$ is the parameter utilized to separate the linear region and the end-state ($\lambda = 0, 1$) transition region. In OSRW and OST simulations, $\theta_O$ should be set as a tiny value so that A is almost 1 and B is almost zero, thus the Jacobian contribution from the $\lambda(\theta)$ function can be negligible. The propagation and the thermolyzation of the $\theta$ particle are based on the Langevin equation, the same as how the $\lambda$ particle is treated in the original $\lambda$-dynamics method.

The OSRW method is based on the modified potential energy function as described in Equation (2). The OSRW algorithm has two recursion components: the recursion kernel to adaptively update $g_m(\lambda, F_\lambda)$ toward its target function $-G_O(\lambda, F_\lambda)$ and the recursion slave to adaptively update $f_m(\lambda)$ toward its target function $-G_O(\lambda)$ based on the concurrent $g_m(\lambda, F_\lambda)$ function. In the original implementation, the metadynamics strategy is employed as the recursion kernel. Specifically, the free energy biased potential $g_m(\lambda, F_\lambda)$ can be obtained by repetitively adding a relatively small Gaussian-shaped repulsive potential as explained in Equation (6).

$$h_o \exp\left(-\frac{|\lambda - \lambda(t_i)|^2}{2w_1^2}\right) \exp\left(-\frac{|F_\lambda - F_\lambda(t_i)|^2}{2w_2^2}\right) \tag{6}$$

which is centered around $[\lambda(t_i), F_\lambda(t_i)]$ at the scheduled update time $t_i$, and thereby discourages the system from often visited configurations. With this procedure repeated, the overall biasing potential shown in Equation (7)

$$g_m(\lambda, F_\lambda) = \sum_{t_i} h_o \exp\left(-\frac{|\lambda - \lambda(t_i)|^2}{2w_1^2}\right) \times \exp\left(-\frac{|F_\lambda - F_\lambda(t_i)|^2}{2w_2^2}\right) \tag{7}$$

will build up and eventually flatten the underlying curvature of the free energy surface in the $(\lambda, F_\lambda)$ space. Then, the free energy profile along the reaction coordinate $(\lambda, F_\lambda)$, which should eventually converge to $-G_O(\lambda, F_\lambda)$, can be estimated as $-g_m(\lambda, F_\lambda)$.

Since for a state $\lambda'$, the free energy profile along its generalized force direction can be estimated as $-g_m[\lambda', F_\lambda(\lambda')]$, the generalized force distribution should be proportional to $\exp\{\beta_O g_m[\lambda', F_\lambda(\lambda')]\}$, in which $\beta_O$ represents $1/(kT_O)$. On the basis of the above discussion, free energy derivatives at each state can be obtained as shown in Equation (8).

$$\left.\frac{dG_o}{d\lambda}\right|_{\lambda'} = \langle F_\lambda \rangle_{\lambda'} = \frac{\int_{F_\lambda} F_\lambda \exp\{\beta_o[g_m(\lambda, F_\lambda)]\} \delta(\lambda - \lambda')}{\int_{F_\lambda} \exp\{\beta_o[g_m(\lambda, F_\lambda)]\} \delta(\lambda - \lambda')} \tag{8}$$

Following the TI formula, the free energy change between the initial state with $\lambda_i$, which is the lower bound of the collective variable range, and any target state with the order parameter $\lambda$ can unfold as a function of $\lambda$ shown in Equation (9).

$$G_o(\lambda) = \int_{\lambda_i}^{\lambda} \frac{dG_o}{d\lambda}\bigg|_{\lambda'} d\lambda' \qquad (9)$$

In the original OSRW implementation, the metadynamics strategy, as described in Equation (7), serves as the recursion kernel, the TI based formula (Equations (8) and (9)) serves as the recursion slave with $f_m(\lambda)$ recursively set as instantaneously estimated $-G_O(\lambda)$.

On the basis of the above OSRW procedure, we carried out a free energy simulation study on the model system. The model simulation was performed on the basis of two-dimensional Langevin dynamics, where the temperature was set as 50 K and the particle mass was set as 100 g/mol. The OSRW simulation led to a converged free energy profile $G_O(x)$ [targeted as $-f_m(x)$], and a converged $-g_m(x, \partial U_O/\partial x)$ (in the model case, $\partial U_O/\partial x$ is the generalized force), where two energy minima are smoothly connected along $\partial U_O/\partial x$ at the transition state region. When converged, this represents the residual free energy surface after the free energy surface flattening treatment $-g_m(x, \partial U_O/\partial x)$ along the order parameter. $[-g_m(x, \partial U_O/\partial x)]$ reveals the fact that the residual free energy barrier exists around the transition state region. It can be traced along $\partial U_O/\partial x$ near the transition state, and more importantly, the residual barrier height (about 2.2 kcal/mol) is similar to that of the hidden energy barrier. In this model system, the generalized force can reveal the direction of the order-parameter-coupled hidden process, this is a prerequisite for efficient and accurate calculations of the target free energy profile $G_O(x)$.

To further understand the role of $\partial U_O/\partial x$ and the difference between the OSRW sampling [e.g., based on $U_O+f_m(x)+g_m(x, \partial U_O/\partial x)$ as in Equation (2)] and the classical generalized ensemble sampling [e.g., based on $U_O+f_m(x)$ as in Equation (1)], we respectively employed the biasing energy functions $f_m(x)$ and $f_m(x)+g_m(x, \partial U_O/\partial x)$, which were obtained in the recursion step, to perform two corresponding equilibrium generalized ensemble simulations. The OSRW sampling allows the system to travel repetitively between two energy minima, as in comparison to the classical generalized ensemble simulation, the system is trapped in the original energy minimum state due to the lack of sampling acceleration along the hidden dimension. Furthermore, according to the umbrella sampling reweighting relationship, the samples collected from the OSRW simulation can be employed to recover the free energy surface along x and y, the well-sampled region of which is the same as the target energy surface. As shown from this recovered free energy surface, the samples are more concentrated along the minimum energy path that connects two energy wells.

In an OSRW simulation, the sampling volume in the orthogonal space increases with the elongation of the simulation length. Additionally, the diffusion sampling overhead around the states, where no hidden barrier exists, continuously increases. As mentioned above, the OSRW method can be generalized to the orthogonal space tempering (OST) algorithm. The target energy function of the OST scheme is described in Equation (3). In the OST scheme, free energy surfaces along the generalized force direction are not completely flattened. Then, the orthogonal space effective sampling temperature $T_{ES}$ can impose an effective sampling boundary to ensure the long-time scale convergence. A larger $T_{ES}$ allows more efficient crossing of hidden free energy barriers but introduces more diffusion sampling overhead.

Interestingly, when $T_{ES}$ approaches the infinity limit, the OST method becomes the original OSRW algorithm; when $T_{ES}$ approaches the system reservoir temperature $T_O$, the second-order GE sampling turns to the first-order GE sampling as described in Equation (1).

The metadynamics method according to the invention achieves adaptive recursions based on a dynamic force-balancing relationship. Its performance strongly depends on energy surface ruggedness and preset parameters. To improve the convergence behavior of OST, in the present work, we designed an alternative method to gain robust recursions.

Among various recursion methods, the adaptive biasing force (ABF) algorithm has a similar efficiency to that of the metadynamics algorithm. In contrast to the metadynamics technique, the ABF method has been mathematically proven; thus the usage of the ABF method as the recursion kernel, specifically via the calculation of the $F_\lambda$-dependent free energy profile $G_O(\lambda', F_\lambda)$ at each $\lambda'$ state, can ensure free energy convergence robustness. A challenging issue remains: how to numerically calculate the generalized force of $F_\lambda$ to estimate target $F_\lambda$-dependent free energy profiles. As a matter of fact, calculating generalized forces of complex order parameters has been known to be a difficult issue in the ABE algorithm implementation. To circumvent this issue, in our OST implementation, we propose a "dynamic reference restraining" (DRR) recursion strategy. Specifically, the target OST potential described above with reference to Equation (3) is rewritten as Equation (10).

$$U_m = U_o(\lambda) + \frac{1}{2}k_\phi(F_\lambda - \phi)^2 + f_m(\lambda) + \frac{T_{ES} - T_o}{T_{ES}} g_m(\lambda, \phi) \qquad (10)$$

in which the generalized force fluctuation is restrained to the move of another dynamic particle $\phi$. In Equation (10), $f_m(\lambda)$ is still targeted toward $-G_O(\lambda)$, and $g_m(\lambda, \phi)$ is targeted toward $-G_O(\lambda, \phi)$, the negative of the free energy surface along $(\lambda, \phi)$ in the canonical ensemble with the energy function $U_O(\lambda) + \frac{1}{2}k (F_\lambda-\phi)2 - G(\lambda)$, where $G(\lambda)$ is the $\lambda$-dependent free energy surface in the canonical ensemble with $U_O(\lambda) + \frac{1}{2}k (F_\lambda-\phi)^2$ as the energy function. On the basis of Equation (10), motions along $F_\lambda$ are indirectly activated via the restraining treatment to the dynamic reference: $\phi$. Here, the dynamics of the $\phi$ particle are also realized through the same extended Hamiltonian method as in $\lambda$-dynamics or $\theta$-dynamics, which was discussed above.

According to the OST target function in Equation (10), we need to design a recursion kernel to estimate $G_O(\lambda, \phi)$ in order to adaptively update $g_m(\lambda, \phi)$. To obtain the two-dimensional function $G_O(\lambda, \phi)$, first, the ABF method is directly employed to calculate the $\phi$ dependent free energy profile at each $\lambda'$ state, specifically on the basis of the following TI relationship shown in Equation 11.

$$G_{o'}(\lambda', \phi) = \int_\phi \left\{ \frac{\partial U_{o'}(\lambda, \phi)}{\partial \phi} \delta(\lambda - \lambda') \right\}_{\phi'} d\phi' \qquad (11)$$

Here, $U_O(\lambda, \phi)$ represents $U_O(\lambda)+\frac{1}{2}k(F_\lambda-\phi)^2$; then $\partial U_{O'}(\lambda,\varphi)/\partial\varphi$ can be simply evaluated as $-k(F_\lambda-\phi)$. It is noted that the numerical boundary of $G_{O'}(\lambda', \phi)$, i.e., the integration boundary in Equation (11), changes as the recursion proceeds. Following the general ABF strategy, $<\partial U_{O'}(\lambda,\varphi)/\partial\varphi\partial(\lambda-\lambda')>\phi'$ can be adaptively estimated as shown in Equation (12).

$$\frac{\sum_i -k_\phi[F_\lambda(t_i)-\phi(t_i)]\delta[\lambda(t_i)-\lambda']\delta[\phi(t_i)-\phi']}{\sum_i \delta[\lambda(t_i)-\lambda']\delta[\phi(t_i)-\phi']} \quad (12)$$

where $t_i$ is the ith scheduled sample-collecting time. Equations (11) and (12) only allow the obtaining of the one-dimension function $G_{O'}(\lambda', \phi)$ at each $\lambda'$ state. The height of the $G_{O'}(\lambda', \phi)$ function can be recalibrated as shown in Equation (13).

$$G_{O''}(\lambda',\phi)=G_{O'}(\lambda',\phi)-G_{O',min}(\lambda',\phi)- \\ RT \ln \int_\phi \exp\left(-\frac{G_{O'}(\lambda',\phi)-G_{O',min}(\lambda',\phi)}{kT_o}\right) \quad (13)$$

where $G_{O'},min(\lambda', \phi)$ is the lowest value in the free energy curve $G_{O'}(\lambda', \phi)$; $G_{O''}(\lambda', \phi)$ represents the post calibration function of $G_{O'}(\lambda', \phi)$. All of the calibrated one-dimension $G_{O''}(\lambda', \phi)$ functions can be assembled to be the target two-dimension $G_O(\lambda, \phi)$ function. Then, $g_m(\lambda, \phi)$ can be adaptively updated as instantaneously estimated $-G_O(\lambda, \phi)$. This calibration procedure is based on the $g_m(\lambda, \phi)$ function definition in Equation (10), specifically to fulfill the condition that the target energy function for $g_m(\lambda, \phi)$ free energy flattening treatment has already been flattened along the $\lambda$ direction. In the DI-OST method according to the invention, Equations (11)-(13) constitute the recursion kernel.

Regarding the recursion slave, the TI formula in Equation (9) is still used to estimate $G_O(\lambda)$; then, $(dG_O/d\lambda)|\lambda'$ at each $\lambda'$ state needs to be evaluated. Different from the recursion in the original OSRW algorithm, where the target function of the recursion kernel is $-G_O(\lambda,F_\lambda)$, here, the target function of the recursion kernel $-G_O(\lambda, \phi)$ does not provide direct information on generalized force $F_\lambda$ distributions. For the fact that $F_\lambda$ is restrained to $\phi$, a simple but an approximate way of estimating $(dG_O/d\lambda)|\lambda'$ can be made on the basis of the assumption of $<\phi>_{\lambda'}=<F_\lambda>_{\lambda'}$. Thus, $(dG_O/d\lambda)|\lambda'$ can be approximated via Equation (14).

$$\frac{dG_o}{d\lambda}\bigg|_{\lambda'} = \langle F_\lambda\rangle_{\lambda'} \approx \langle \phi\rangle_{\lambda'} = \frac{\int_\phi \phi \exp\{\beta[g_m(\lambda,\phi)]\}\delta(\lambda-\lambda')}{\int_\phi \exp\{\beta[g_m(\lambda,\phi)]\}\delta(\lambda-\lambda')} \quad (14)$$

To more rigorously estimate $(dG_O/d\lambda)|\lambda'$, $G_O(\lambda',F_\lambda)$ needs to be calculated for each $\lambda'$ state as described above. Notably, the samples collected at the state $\lambda'$ with $F_\lambda=F_{\lambda'}$ can be considered as being obtained from multiple independent ensembles, each of which corresponds to a unique restraining reference value $\phi'$. According to the umbrella integration relationship, based on the samples from each $(\lambda', \phi')$ restraining ensemble, $(dG_O(\lambda',F_\lambda)/dF_\lambda)|F\lambda',\lambda'$ can be estimated as $1/(\beta_O)(F_\lambda'-\overline{F_\lambda^{\lambda',\phi}})/(\sigma_\lambda^{\lambda',\phi'})^2-k_\phi(F_\lambda'-\phi')$, where $\overline{F_\lambda^{\lambda,\phi}}$ stands for the average of the $F_\lambda$ values of all of the samples in the $(\lambda', \phi')$ restraining ensemble and $\sigma_\lambda^{\lambda',\phi'}$ represents the variance of samples. Using the multihistogram approach to combine the estimations from all of the restraining ensembles that are visited at the $\lambda'$ state, $(dG_O(\lambda',F_\lambda)/dF_\lambda)|F\lambda',\lambda'$ can be calculated as shown in Equation (15).

$$\frac{dG_o(\lambda',F_\lambda)}{dF_\lambda}\bigg|_{F_\lambda',\lambda'} = \frac{\int_{\phi'}\rho(\phi'_{\lambda',F_\lambda'})\left[\frac{1}{\beta_o}\frac{F_\lambda'-\overline{F_\lambda^{\lambda',\phi'}}}{(\sigma_\lambda^{\lambda',\phi'})^2}-k_\phi(F_\lambda'-\phi')\right]}{\int_{\phi'}\rho(\phi'_{\lambda',F_\lambda'})} \quad (15)$$

where $\rho$(where $\rho(\phi \lambda',F\lambda')$ denotes the total number of the $(\lambda',F_\lambda)$ samples that are collected from the $\phi'$ restraining ensemble.

Then, based on the TI relationship, $G_O(\lambda',F_\lambda)$ can be calculated according to Equation (16).

$$\left|G_{O'}(\lambda',F_\lambda)=\int_{F_\lambda'}\frac{dG_o(\lambda',F_\lambda)}{dF_\lambda}\bigg|_{F_\lambda',\lambda'}dF_\lambda' \quad (16)$$

Again, like in Equation (11), the numerical boundary of $G_O(\lambda',F_\lambda)$, i.e., the integration boundary in Equation (16), changes as the recursion proceeds. Following the corresponding derivation in the original OSRW method, we can obtain $(dG_O/d\lambda)|\lambda'$ at the state $\lambda'$ using Equation 17.

$$\frac{dG_o}{d\lambda}\bigg|_{\lambda'} = \langle F_\lambda\rangle_{\lambda'} = \frac{\int_{F_\lambda} F_\lambda \exp\{-\beta_o[G_{O'}(\lambda,F_\lambda)]\}\delta(\lambda-\lambda')}{\int_{F_\lambda} \exp\{-\beta_o[G_{O'}(\lambda,F_\lambda)]\}\delta(\lambda-\lambda')} \quad (17)$$

On the basis of the corresponding TI formula in Equation (9), $f_m(\lambda)$, which is targeted as $-G_O(\lambda)$, can then be adaptively updated. In the DI-OST method according to the invention, Equations (15)-(17) and (9) constitute the recursion slave. Notably, $f_m(\lambda)$ does not have to be equal to $-G_O(\lambda)$ in a strict manner. Here, it is highly recommended to employ the approximate approach based on Equations (11)-(14) and (9) to update $f_m(\lambda)$, and the more rigorous approach based on Equations (15)-(17) and (9) to estimate $G_O(\lambda)$, because of the fact that $<\phi>\lambda'$ in Equation (14), is directly estimated from $\phi$-space ABF calculations (Equations (11) and (12)) and should converge faster. In the DI-OST method, both the recursion kernel and the recursion slave are based on the integration schemes. Therefore, it is named the double-integration recursion method.

The double-integration recursion based OST method is implemented in the "orthogonal space sampling module", which is currently coupled with our customized CHARMM program. See, Brooks, B. R.; Bruccoleri, R. E.; Olafson, B. D.; States, D. J.; Swaminathan, S.; Karplus, M. CHARMM: A program for macromolecular energy, minimization, and dynamics calculations. J. Comput. Chem. 1983, 4, 187-217 and Brooks, B. R.; Brooks, C. L.; Mackerell, A. D.; Nilsson, L.; Petrella, R. J.; Roux, B.; Won, Y.; Archontis, G.; Bartels, C.; Boresch, S.; Calfisch, A.; Caves, L.; Cui, Q.; Dinner, A. R.; Feig, M. Feig; Fischer, S.; Gao, J.; Hodoscek, M.; Im, W.; Kuczera, K.; Lazaridis, T.; Ma, J.; Ovchinnikov, V.; Paci, E.; Pastor, R. W.; Post, C. B.; Pu, J. Z.; Schaefer, M.; Tidor, B.; Venable, R. M.; Woodcock, H. L.; Wu, X.; Yang, W.; York, D. M.; Karplus, M. CHARMM: The biomolecular simulation program. J. Comput. Chem. 2009, 30, 1545-1614. CHARMM is available from Harvard University.

In the present invention, the following van der Waals soft-core potential form is employed to treat the atoms which are annihilated as illustrated in Equation (18).

$$U_{\text{"softcore"}vdW} = (1-\lambda)\left[\frac{A}{(\alpha_{vdW}\lambda^2 + r^6)^2} - \frac{B}{\alpha_{vdW}\lambda^2 + r^6}\right] \quad (18)$$

where $\alpha_{vdW}$ is the van der Wools soft-core shifting parameter. It is noted that Equation (18) is different from the one in the currently released CHARMM program. The electrostatic soft-core potential is based on Equation (19).

$$U_{\text{"softcore"}elec} = \frac{(1-\lambda)Q_A Q_B}{\sqrt{\alpha_{elec}\lambda + r^2}} \quad (19)$$

where $\alpha_{elec}$ is the electrostatic soft-core shifting parameter. In Equations (18) and (19), the annihilation is assumed to occur at the state of $\lambda=1$; to be consistent, in this study, all of the dummy atoms are set at the state of $\lambda=1$.

In the present invention, the DI-OST method is demonstrated in the context of alchemical free energy simulation, specifically to calculate the free energy difference between benzyl phosphonate and difluorobenzyl phosphonate in aqueous solution, to estimate the solvation free energy of the octanol molecule, and to predict the Barnase-Barstar nontrivial binding affinity change induced by the Barnase N58A mutation.

The molecules of benzyl phosphonate (BP) and difluorobenzyl phosphonate (F2BP) are the side chain analogues of prototypical phosphotyrosine mimetics, which are common targets in drug discovery. The free energy difference between these two molecules in aqueous solution, $\Delta G_{BP \rightarrow F2BP}^{aqueous}$, has been used as a test-bed to analyze free energy simulation methods. In practical studies, if combined with the free energy difference in gas phase $\Delta G_{BP \rightarrow F2BP}^{gas}$, $\Delta G_{BP \rightarrow F2BP}^{aqueous} - \Delta G_{BP \rightarrow F2BP}^{gas}$ gives rise to the value of the solvation energy difference; if combined with the free energy difference in a protein binding site $\Delta G_{BP \rightarrow F2BP}^{protein}$, $\Delta G_{BP \rightarrow F2BP}^{protein} - \Delta G_{BP \rightarrow F2BP}^{aqueous}$ gives rise to the value of the binding free energy difference. Here, the test calculations on $\Delta G_{BP \rightarrow F2BP}^{aqueous}$ gives rise to the value of the binding free energy difference. Here, the test calculations on $\Delta GBP \rightarrow F2BP$ aqueous calculations on $\Delta G_{BP} \rightarrow F2BP^{aqueous}$ are used to comparatively evaluate the original OSRW method and the invention's DI-OST method in the aspects of algorithm robustness and long-time convergence. On the basis of each of the two methods, five sets of independent simulations were carried out.

The MD simulation setup was the same as the one in the earlier studies, where the BP and F2BP molecules are described with the CHARMM22 parameter. In total, 294 water molecules are included in the truncated octahedral box; the water molecules are treated with the TIP3P model. The diagram below shows the setup of the alchemical transition from BP to F2BP.

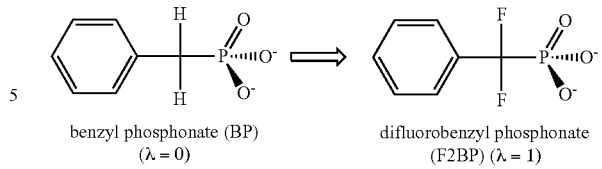

benzyl phosphonate (BP) ($\lambda = 0$)   difluorobenzyl phosphonate (F2BP) ($\lambda = 1$)

For the fact that there is no vanishing atom in either of the end states, the linear hybrid energy function (as described by Equation (4)) is used in this model study.

In the five OSRW simulations, $g(\lambda, F_\lambda)$ (in Equation (7)) was updated every 10 time steps; the height of the Gaussian function h was set as 0.01 kcal/mol; the widths of the Gaussian function, $\omega 1$ and $\omega 2$, were set as 0.01 and 4 kcal/mol respectively, and $f_m(\lambda)$ was updated (based on Equations (8) and (9)) once per 1000 time steps. In the five DI-OST simulations, the samples were collected every time step, $g(\lambda, \phi)$ was updated (based on Equations (11)-(13)) once per 1000 time steps, $f_m(\lambda)$ was updated (based on Equations (17-19) and (9)) once per 1000 time steps, and $T_{ES}$ was set as 600 K (the system reservoir temperature is 300 K). The length of each simulation is 20 nanoseconds (ns).

The model calculation on the octanol solvation free energy is to understand the role of the orthogonal space sampling temperature $T_{ES}$. The octanol molecule which is described by the CHARMM general force field (CGFF), is embedded in a truncated octahedral water box with a total of 713 TIP3P water molecules. In the alchemical free energy simulation setup, the solvated octanol molecule ($\lambda=0$) is changed to a gas phase molecule ($\lambda=1$), which does not have any interaction with the solvent molecules. Accordingly, all of the van der Waals and the electrostatic energy terms describing the solute-solvent interactions are subject to the soft-core treatment, in which $\alpha_{vdW}$ is set as 0.5 and $\alpha_{elec}$ is set as 5.0. Then, the solvation free energy of octanol $G_{octanol}^{solvation}$ can be estimated as the negative of the free energy difference $-\Delta G_\lambda=0 \rightarrow \lambda=1$ between the two end states.

To understand the influence of $T_{ES}$ on sampling efficiency, two sets of independent DI-OST simulations were run, each of which includes eight simulations with $T_{ES}$ respectively set as 750 and 375 K (the system reservoir temperature is 300 K). The samples were collected every time step. $gm(\lambda, \phi)$ was updated (based on Equations (11)-(13)) once per 1000 time steps. $f_m(\lambda)$ was also updated (based on Equations (17-19) and (9)) once per 1000 time steps. The length of each simulation is 17 ns.

The model study on the binding between barnase, an extracellular RNase of *Bacillus amyloliquefaciens*, and barstart, the intracellular polypeptide inhibitor of barnase demonstrates the DI-OST method in predicting mutation induced protein-protein binding affinity changes. The barnase N58A mutation is located at the second layer of the binding interface; this noncharging mutation causes about 3.1 kcal/mol of the binding affinity loss.

The DI-OST simulations were performed to calculate the alchemical free energy changes in two environments: $\Delta G_{Asn \rightarrow Ala}^{complex}$ in the barnase-barstar complex and $\Delta G_{Asn \rightarrow Ala}^{barnase}$ in the unbound barnase. The binding affinity change $\Delta \Delta G_{Asn \rightarrow Ala}$ can be calculated as $\Delta G_{Asn \rightarrow Ala}^{complex} - \Delta G_{Asn \rightarrow Ala}^{barnase}$. All of the systems are treated with the CHARMM27/CMAP model. In the model for the $\Delta G_{Asn \rightarrow Ala}^{complex}$ calculation, the barnase-barstar complex (with the PDB code of 1BRS) is embedded in the octahedral box with 18 902 water molecules; in the model for the $\Delta G_{Asn \to Ala}^{barnase}$ calculation, the unbound barnase (also based on the PDB code of 1BRS) is embedded in the octahedral box with 11 291 water molecules.

In the alchemical free energy simulation setup shown in the diagram below, the vanishing atoms in Asn58 ($\lambda=0$) are switched to the corresponding dummy atoms at $\lambda=1$. The bond, angle, and dihedral terms associated with the dummy atoms are set identical to the corresponding ones of the original asparagine residue. All of the van der Waals terms and the electrostatic energy terms associated with the dummy atoms are subject to the soft-core treatment, in which $\alpha_{vdW}$ was set as 0.5 and $\alpha_{elec}$ was set as 5.0. The three DI-OST simulations were performed with $T_{ES}$ set as 1500 K (the system reservoir temperature is 300 K); the samples were collected every time step $g(\lambda, \phi)$ was updated (based on Equations (11-13)) once per 1000 time steps. $f_m(\lambda)$ was also updated (based on Equations (17-19) and (9)) once per 1000 time steps.

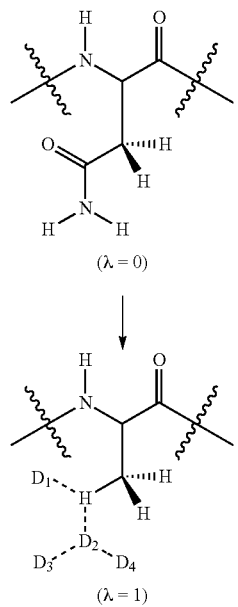

The CGFF parameters were generated through the CHARMM-GUI server. The particle mesh ewald (PME) method63 was applied to take care of the long-range columbic interactions while the short-range interactions were totally switched off at 12 Å. The Nóse-Hoover method was employed to maintain a constant reservoir temperature at 300 K, and the Langevin piston algorithm was used to maintain the constant pressure at 1 atm. The time step was set as 1 fs.

The results from one of the five DI-OST simulations are summarized as follows. In about 800 ps, the scaling parameter $\lambda$ completed the first one-way trip, which started at $\lambda=0$. It is noted that free energy estimations are only possible when the sampling covers the entire $\lambda$ space. At 820 ps, the initial estimation of $\Delta G_{BP \to F2BP}^{aqueous}$ gives 299.91 kcal/mol, which is very close to the finally converged result 299.77 kcal/mol. In the DI-OST scheme, the $((T_{ES}-T_O)/T_{ES})$ $g_m(\lambda, \phi)$ biasing term enables the accelerating of $\phi$ moves, which through the restraint term $\frac{1}{2}k_\phi (F_\lambda-\phi)^2$ induces simultaneous fluctuation enlargement of the generalized force $F_\lambda$. In these simulations, the restraint force constant k was set as 0.1 (kcal/mol)$^{-1}$; $F_\lambda$ and $\phi$ are robustly synchronized. The recursive orthogonal space tempering treatment allows $F_\lambda$ fluctuations to be continuingly enlarged until around 8 ns; then the $\phi$ space sampling boundary imposed by $T_{ES}$ was reached. Subsequent recursion kernel and recursion slave updates enable continuous refinement of the $g_m(\lambda, \phi)$ and $f_m(\lambda)$ terms. At the end of the 20 ns simulation, the orthogonal space sampling temperature 600 K allows the fluctuations of $\phi$ and $F_\lambda$ to overcome ~9 KT strongly coupled free energy barriers that are hidden in the orthogonal space.

The BP and D2BP molecules differ only in their local polarity. One would expect moderate environment changes to be associated with the target alchemical transition; simulating the BP-D2BP transition may not fully demonstrate the sampling power of the DI-OST method. However, for its simplicity, this is an ideal system to test the robustness and the long-time convergence behavior of a free energy simulation method. The estimated free energies from the five DI-OST simulations converge to the average value of 299.77 kcal/mol, which quantitatively agrees with the results obtained from the classical free energy simulation studies. Notably, as mentioned above, in this model study, we only targeted our calculations on the estimation of the alchemical free energy difference, $\Delta G_{BP \to F2BP}^{aqueous}$, the value of which alone does not have any physical meaning. With 20 ns of the simulation lengths, the variance of the five independently estimated values is as low as 0.01 kcal/mol. Within only 940 picoseconds (ps), all five DI-OST simulations had completed their first one-way trips. Then, the average of the estimated values is 299.82 kcal/mol, and the variance of the calculation results is 0.12 kcal/mol. In 2 ns, the average of the estimated values converges to 299.79 kcal/mol, and the variance of the calculation results is 0.04 kcal/mol. In DI-OST simulations, $G_O(\lambda)$ [the negative of $f_m(\lambda)$] should converge faster than $G_O(\lambda, \phi)$ [the negative of $g_m(\lambda, \phi)$] because of the fact that the free energy derivative $dG_O(\lambda)/d\lambda$ is largely determined by the lower region of the free energy surface along $(\lambda, F_\lambda)$. Besides the sampling efficiency, the DI-OST method provides free energy estimation robustness and long-time convergence rigorousness.

As discussed above, the original OSRW method is limited in two aspects. First, the orthogonal space sampling temperature $T_{ES}$ is effectively infinity; thus, there is no boundary to restrict the magnitude of $F_\lambda$ fluctuation enlargement. The orthogonal space free energy surface flattening treatment enlarges $F_\lambda$ fluctuations boundlessly. In comparison with the DI-OST simulations, which have their sampling boundaries imposed by the finite $T_{ES}$ value (600 K), the OSRW simulations have ever-increasing sampling coverage. Consequently, both the average and the variance of the free energy results show time-dependent oscillatory behaviors. Second, the original OSRW method is based on the metadynamics recursion kernel. The metadynamic kernel provides extra dynamic boosts on $\lambda$ moves. Then, the first one-way trips can be quickly completed (around 350 ps in average). Although the free energy estimations could be started earlier, both of the short-time and long-time convergence behaviors of the OSRW simulations are not nearly as good as those of the DI-OST simulations. For example, at 2 ns, the average of the free energy values from the OSRW simulations converges to 299.97 kcal/mol, and the variance of these results is about 0.10 kcal/mol. The metadynamics sampling in the OSRW simulations is by nature in the nonequilibrium regime; in comparison, the sampling in the DI-OST simulations starts in the near-equilibrium regime and rigorously approaches the equilibrium regime with the converging of the two recursion target functions. The robustness and the convergence behavior of OSRW simulations can be improved with the decreasing of the employed Gaussian height; however, it is expected that then the orthogonal space recursion (the recursion kernel) efficiency will be lower and the $g_m(\lambda, F_\lambda)$ convergence will be slower.

The DI-OST algorithm allows the orthogonal space sampling strategy to be more robustly realized for free energy simulations. It should be noted that although in the above comparison, better robustness and long-time convergence behavior of the DI-OST simulations have been demonstrated; indeed, within the simulated time scale, the absolute performance of the OSRW simulations is also expected to be superior.

Among various alchemical free energy simulation applications, solvation free energy calculations are unique because of the fact that they may require extensive sampling but the results are still quantitatively verifiable by classical free energy simulations. In this study, we carried out solvation energy calculations on the octanol molecule to understand the role of the orthogonal space sampling temperature $T_{ES}$ in the DI-OST method.

As discussed above, the sampling length required to achieve the first one-way trip is a key factor in sampling efficiency measurement. The average of the first one-way trip sampling lengths in the eight $T_{ES}$=750 K DI-OST simulations is 1.6 ns; the variance of these sampling lengths is 0.53 ns. In comparison, the average of the first one-way trip sampling lengths in the eight $T_{ES}$=375 K DI-OST simulations is 3.57 ns, and the variance of the first one-way trip sampling lengths is 0.63 ns. The sampling bottleneck is located in the region of $\lambda \in (0.7, 0.8)$; infrequent crossing of this region slows down overall $\lambda$ round-trip diffusivity. The solute appearance/annihilation transition is the major event in this sampling bottleneck region.

It is noted that due to the employment of the soft-core potential, the solute appearance/annihilation transition is shifted from $\lambda$=1, the expected region when the linear hybrid alchemical potential is applied, to this new region. Solvent molecule reorganizations are the "hidden" events that are associated with solute insertions/annihilations. When the orthogonal space sampling temperature $T_{ES}$ is higher (for example 750 K), the magnitude of the $F_\lambda$ fluctuation is expected to be larger and hidden free energy barriers associated with solvent reorganizations can be more quickly crossed; thereby, the sampling of the bottleneck region can be more efficient.

With regard to the time-dependent averages of the estimated desolvation free energies from the eight $T_{ES}$=750 K DI-OST simulations, and the time-dependent variances of the estimated desolvation free energies from the eight $T_{ES}$=750 K DI-OST simulations, at around 2 ns, the average of the estimated values is 3.45 kcal/mol and the variance of these values is about 0.23 kcal/mol. At around 6 ns, the average of the estimated values drops to around 3.35 kcal/mol, while their variance decreases to 0.17 kcal/mol. At around 13.5 ns, the free energy estimations reach very nice convergence with the average value of 3.36 kcal/mol, and the estimation variance drops below 0.1 kcal/mol. By the inclusion of the long-range Lennard-Jones correction (0.79 kcal/mol), the predicted solvation energy, −4.15±0.1 kcal/mol, is in excellent agreement with the experimental value −4.09 kcal/mol. At 17 ns, a nicely converged $g_m(\lambda, \phi)$ function was obtained with the variance further reduced to 0.08 kcal/mol.

The orthogonal space sampling temperature 750 K allows the fluctuations of $\phi$ and $F_\lambda$ to quickly escape ~5 kT strongly coupled free energy barriers. In comparison, the eight $T_{ES}$=350K DI-OST simulations have smaller sampling coverage in the orthogonal space. The lack of sampling in the orthogonal space not only leads to the longer sampling length requirement for the first one-way trips as discussed above but also leads to the slower convergence. At 17 ns, some of the $T_{ES}$=350 K DI-OST simulations have not yet converged well because of the fact that the variance among them is still larger than 0.1 kcal/mol. As a result, the average of these values is about 0.05 kcal/mol away from the average of the values estimated from the $T_{ES}$=750K simulations. With $T_{ES}$=350 K, the orthogonal space sampling treatment temperature 350 K only allows the fluctuations of $\phi$ and $F_\lambda$ to escape less than 2 kT strongly coupled hidden free energy barriers.

As shown in the above analysis, the orthogonal space tempering treatment allows the sampling bottleneck regions, where hidden free energy barriers exist, to be more efficiently explored. If there is no hidden free energy barrier in the orthogonal space, a higher orthogonal space sampling temperature $T_{ES}$ may introduce more diffusion sampling overhead, which might lower free energy estimation precision. In practical biomolecular simulation studies, there usually exist large hidden free energy barriers, and then, obtaining accurate free energy estimation should be a higher priority than improving estimation precision, as long as the estimation precision is in a reasonable range. On the basis of our experience, when a new system is explored, we would like to recommend setting $T_{ES}$ in a range between 750 and 1500K.

It has been known that charge-charge interactions are directly responsible for the strong binding between Barnase and Barstar. The Barnase Asn58 residue is located at the second layer of the binding interface. As measured experimentally, the noncharging N58A mutation causes 3.1 kcal/mol of the binding affinity loss. This unusual electrostatic response suggests that nontrivial conformational changes are likely to be coupled with the N58A mutation. To quantitatively understand the N59A induced binding affinity change, a specialized technique like the DI-OST method should be applied to ensure adequate sampling of the coupled structural transitions. To confidently sample such conformational changes, in the DI-OST simulations, $T_{ES}$ is set at 1500 K.

Two DI-OST simulations, which are respectively based on the Barnase-Barstar (bound) complex structure and the Barnase (unbound) structure, were performed. In 4 ns, multiple $\lambda$ round-trips were realized in both of the DI-OST simulations. It took the bound-state simulation only 1.1 ns to complete the first one-way trip, while it took the unbound-state sampling about 1.8 ns to cover the entire order parameter range. The dynamics of the scaling parameter $\lambda$ in the unbound-state simulation reveals that the region of $\lambda$=0.4 is the sampling bottleneck area, where slow gating events need to occur for $\lambda$ continuing travels. In 4 ns, good convergence was realized in both of the free energy simulations. Through the DI-OST recursion treatment, the $\lambda$-dependent free energy derivatives $dG_O/d\lambda$ were calculated; the binding affinity change $\Delta\Delta G_{Asn \to Ala}$ is largely responsible for the difference that occurs near the alanine state ($\lambda$=1), where the two free energy derivative curves are distinct from each other. As discussed below, the conformational change of the mutated (N58A) Barnase induced by the binding/unbinding of Barstar is mainly responsible for $\Delta\Delta G_{Asn \to Ala}$. On the basis of the TI formula (Equation (9)), $\Delta G_{Asn \to Ala}^{complex}$ is estimated to be 94.0 kcal/mol and $\Delta G_{Asn \to Ala}^{Barnase}$ is estimated to be 91.1 kcal/mol; thus $\Delta\Delta G_{Asn \to Ala}$ can be predicted to be 2.9 kcal/mol, which is in excellent agreement with the experimental value of 3.1 kcal/mol. The orthogonal space tempering treatment allows the fluctuations of φ and $F_\lambda$ to overcome ~12-14 kT of the strongly coupled hidden free energy barriers.

The comparison of the crystal structures (1BRS and 1BNR) suggests that the Barnase protein has the identical conformation at the bound and the unbound states. The Barnase Asn58 is located on a Barstar-binding loop, but at the opposite side from the binding interface residues, for instance, Arg59. In these structures, the binding interface region on the Arg59-containing loop is zipped by the hydrogen bond between the amide group of Gly61 and the carbonyl group of Asn58; thereby Arg59 can be accurately positioned into the binding site. This zipped structure is further locked by two additional hydrogen bonds between the Asn58 side chain and the backbone amide/carbonyl groups. In the bound-state DI-OST simulation, with residue 58 repeatedly interconverted between the two end chemical states: asparagine and alanine, the structure of the Arg59-containing loop stayed unchanged, even when λ approached the alanine state (λ=1). The hydrogen bond between the amide group of Gly61 and the carbonyl group of Asn58 was not broken during the entire simulation. The fluctuation of the distance between residues 58 and 63 was modest. In contrast, in the unbound-state simulation, synchronously with the λ move, the Arg59-containing loop varied back and forth between the original zipped conformation (at the asparagine state when λ=0) and a newly formed unzipped conformation (at the alanine state when λ=1). When residue 58 turned to alanine, the distance between residues 58 and 63 increased, and when λ traveled back to the asparagine state, the canonical hydrogen bonds between these two residues were formed again. Correspondingly, the zipping hydrogen bond repetitively broke and reformed. On the unzipped loop of the unbound N59A mutant, Arg59 flips away from its wild-type gesture that is originally preorganized to bind Barstar.

The above analysis suggests that there is strong coupling between the Barnase-Barstar binding and the Arg59-containing loop zipping, and Asn58 plays a pivotal role in prestabilizing the zipped conformation of the Arg59-containing loop when Barnase is in the unbound state. Therefore, the Barnase-Barstar binding can be enhanced. When Asn58 is mutated to alanine, the Arg59-containing loop in the unbound Barnase is unzipped due to the loss of both the locking hydrogen bonds by Asn58 and the binding of the Barstar. When the N58A mutant binds Barstar, some free energy penalty needs to be paid in order to form the bound conformation, which, as revealed by the bound state DI-OST simulation, stays zipped in the Barstar-bound state regardless of the existence of Asn58. The two simulations share the similar free energy derivative curves near the asparagine (λ=0) state; this indicates that there is only modest contribution from the direct electrostatic interaction difference to the binding affinity change. In essence, the binding affinity change induced by the N58A mutation is largely responsible for the mutation-induced conformational change at the unbound state. The DI-OST method allows the corresponding conformational change to be synchronously sampled with the λ moves; therefore, the binding affinity change can be efficiently predicted.

The simulations described above were performed using a 16-core Intel 3.2 GHz cluster. However, as discussed below, other computing platforms may be preferred.

With reference to FIG. 1, in one embodiment, the invention 100 is realized with the implementation of two software-based engines: a molecular dynamics (MD) engine 135 and an orthogonal space tempering (OST) engine 105. The molecular dynamics engine 135 provides a computer simulation method for studying the physical movements of atoms and molecules, wherein the atoms and/or molecules are allowed to interact for a fixed period of time, thereby providing a view of the dynamic evolution of the system. The orthogonal space tempering engine 105 implements the above-derived orthogonal space recursion and propagation calculations. The molecular dynamics engine 135 is implemented in a first CPU or GPU and the orthogonal space tempering engine 105 is implemented in a second CPU or GPU, which is independent form the first CPU or GPU. In a particular embodiment, the molecular dynamics engine 135 is a modified version of Chemistry at HARvard Macromolecular Mechanics (CHARMM) and the orthogonal space tempering engine 105 is a modified version of FLOSS. The FLOSS software can be obtained from Florida State University.

In operation, an input generator 130 provides initialization inputs to the molecular dynamics engine 135 operating in the first GPU or CPU, which then passes the initialization input to an input interpreter 140. The input interpret interpreter 140 sends some of the inputs to the OST engine 105 to initialize the OST environment 110 operating in the second GPU or CPU. The OST engine and the molecular dynamics engine operate in parallel and pass information between each other, illustrated. At each molecular dynamics propagation step performed by the molecular dynamics propagation engine 145, the OST engine 110 feeds forces, which are generated by the orthogonal space recursion and propagation calculation engine 115 based on the OST recursion protocol, into the molecular dynamics engine 135 so that molecular motions will be altered from regular molecular dynamics behaviors. Altering the molecular motions by speeding-up the structural changes of the proteins, based upon the physics-based algorithm of the present invention, allows free energy barriers in the orthogonal space to be automatically overcome. Additionally, at each molecular dynamics propagation step, the OST engine 110 propagates the motions of the virtual molecules, the values of which are used in the generation of the forces to be fed to the molecular dynamics engine 135. In addition, at each step, the OST engine 110 also acquires samples from the molecular dynamics engine 135 to perform its data recursion operation. The OST engine 110 provides output 120 independent from the output 165 of the molecular dynamics engine 135 and has its own data structure for saving data to be used in its own adaptive recursive operations. The propagation steps of the OST engine 125 and the molecular dynamics engine 150 continue for a predetermined period of time, as previously discussed. The outputs can be used to predict the most viable new drug candidates.

The OST engine output includes four data files called dvdl.dat, flc.dat, free.dat, and g2d.pm3d.dat. The file "dvdl.dat" gives the time-dependent parameter changes. The file "flc.dat' gives the current free energy related information. The file "free.dat" gives the time-dependent estimated free energy values. The file "g2d.pm3d.dat" gives the orthogonal space free energy surface information.

In general, the OST engine 110 of the present invention is designed as an external machine, which has its own stand-alone internal operations that are effective in speeding-up the sampling speed in comparison to that of the molecular dynamics engine 135. The OST engine 110 has been implemented in both CPU and GPU environments to work with both CPU and GPU based molecular dynamics engine 135. The OST engine 110 has been designed to be flexibly plugged into a standard molecular dynamics engine 135.

Figure 2:
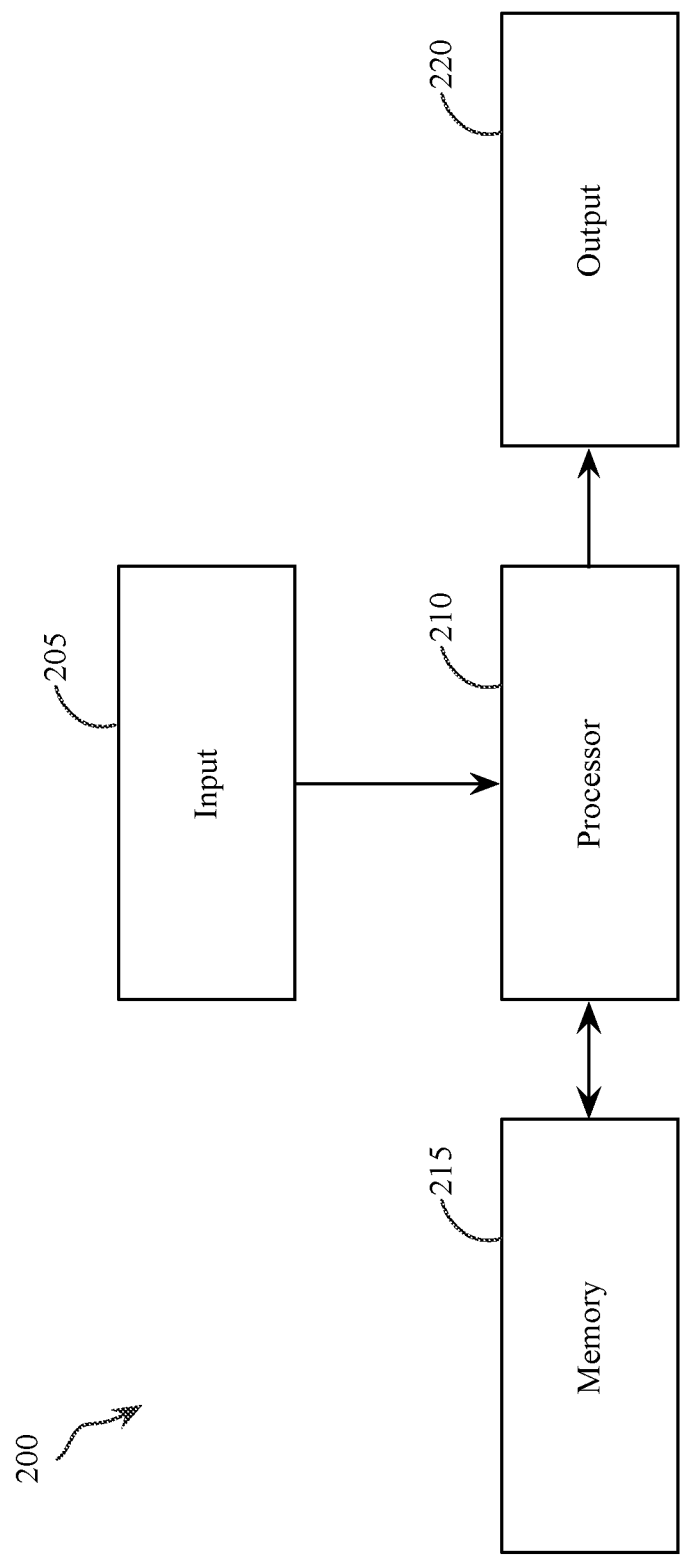
FIG. 2 is a high level block diagram illustrating an apparatus for carrying out the invention.

Turning now to FIG. 2, an apparatus 200 for implementing the OST device of the present invention includes a processor 210 with associated memory 215, an input 205 and an output 220. As mentioned above, the test simulations were performed with a 16-core Intel 3.2 GHz cluster. However, it is believed that other computing platforms may be preferred. In particular, it is believed that GPUs are more powerful in implementing the invention than CPUs. The NVIDIA GPU platform (http://www.nvidia.com/object/gpu-applications.html) is the presently preferred platform.

There have been described and illustrated herein several embodiments of methods and apparatus for double-integration orthogonal space tempering. While particular embodiments of the invention have been described, it is not intended that the invention be limited thereto, as it is intended that the invention be as broad in scope as the art will allow and that the specification be read likewise. It will therefore be appreciated by those skilled in the art that yet other modifications could be made to the provided invention without deviating from its spirit and scope as claimed.

The invention claimed is:

1. A computer-implemented method for identifying one or more potentially therapeutic drug candidates by simulating systems of molecules through molecular dynamics, the method comprising:

initializing a molecular dynamics engine in a first CPU or GPU;

initializing an orthogonal space tempering (OST) engine in a second CPU or GPU, wherein the first CPU or GPU is independent of the second CPU or GPU;

at each of a plurality of propagation steps of the molecular dynamics engine;

determining, by the orthogonal space tempering (OST) engine, an alchemical free energy of a system comprising one or more ligands and a specific receptor in an orthogonal space by performing orthogonal space tempering utilizing a second-order generalized ensemble, wherein the second-order generalized ensemble is a generalized orthogonal space random walk (OSRW) method having an effective sampling boundary imposed by a pre-selected orthogonal space sampling temperature ($T_{ES}$) and described by a modified energy function as $$U_m = U_o(\lambda) + f_m(\lambda) + \frac{T_{ES} - T_0}{T_{ES}} g_m(\lambda, F_\lambda)$$

where $\lambda$ is an alchemical order parameter, $U_O(\lambda)$ stands for a hybrid energy function that is constructed on the basis of the constraints of $U_0(0)=U^A$ and $U_1(0)=U^B$, wherein two ends states A and B respectively represented by $\lambda=1$ and $\lambda=0$, $f_m(\lambda)$ is adaptively updated to approach $-G_0(\lambda)$, $g_m(\lambda,F_\lambda)$ is adaptively updated to approach $-G_0(\lambda, F_\lambda)$ and the contribution of $g_m(\lambda,F_\lambda)$ is scaled by a parameter $$\frac{(T_{ES} - T_0)}{T_{ES}},$$

wherein $T_0$ is a system reservoir temperature and $T_{ES}$ is a present parameter referred to as the orthogonal space sampling temperature;

determining, by the orthogonal space tempering (OST) engine one or more forces between the one or more ligands and the specific receptor based upon the alchemical free energy of the system;

providing the one or more forces to the molecular dynamics engine to accelerate the speed of the structural change of the one or more ligands to overcome one or more free energy barriers in the orthogonal space;

generating, by the OST engine, a first file storing time-dependent free energy parameter changes associated with the alchemical free energy of the system;

generating, by the OST engine, a second file storing current data associated with the alchemical free energy of the system;

generating, by the OST engine, a third file storing time-dependent energy values associated with the alchemical free energy of the system;

generating, by the OST engine, a fourth file storing orthogonal space free energy surface data associated with the alchemical free energy of the system;

predicting, based on at least one of the first file, the second file, the third file, and the fourth file, one or more chemical state related thermodynamic properties of the system based upon the determined alchemical free energy of the system; and identifying one or more potentially therapeutic drug candidates by identifying one or more ligands that are most likely to bind strongly to the specific receptor based upon the predicted one or more chemical state related thermodynamic properties of the system.

2. The method according to claim 1, wherein performing orthogonal space tempering further comprises, performing double-integration recursion.

3. The method according to claim 2, wherein:
the double-integration recursion is based on dynamic reference restraining.

4. The method according to claim 1, wherein:
the method further provides an output selected from the group consisting of, a molecular trajectory and the alchemical free energy of the system.

5. An apparatus for one or more potentially therapeutic drug candidates, the apparatus comprising:

a molecular dynamics engine in a first CPU or GPU;

an orthogonal space tempering (OST) engine in a second CPU or GPU, wherein the first CPU or GPU is independent of the second CPU or GPU;

at each of a plurality of propagation steps, the orthogonal space tempering (OST) engine configured to;

determine an alchemical free energy of a system comprising one or more ligands and a specific receptor in an orthogonal space by performing orthogonal space tempering utilizing a second-order generalized ensemble, wherein the second-order generalized ensemble is a generalized orthogonal space random walk (OSRW) method having an effective sampling boundary imposed by a pre-selected orthogonal space sampling temperature ($T_{ES}$) and described by a modified energy function as $$U_w = U_o(\lambda) + f_m(\lambda) + \frac{T_{ES} - T_0}{T_{ES}} g_m(\lambda, F_\lambda)$$

where $\lambda$ is an alchemical order parameter, $U_O(\lambda)$ stands for a hybrid energy function that is constructed on the basis of the constraints of $U_0(0)=U^A$ and $U_1(0)=U^B$, wherein two ends states A and B respectively represented by $\lambda=1$ and $\lambda=0$, $f_m(\lambda)$ is adaptively updated to approach $-G_0(\lambda)$, $g_m(\lambda,F_\lambda)$ is adaptively updated to approach $-G_0(\lambda, F_\lambda)$ and the contribution of $g_m(\lambda,F_\lambda)$ is scaled by a parameter $$\frac{(T_{ES}-T_0)}{T_{ES}},$$

wherein $T_0$ is a system reservoir temperature and $T_{ES}$ is a present parameter referred to as the orthogonal space sampling temperature;
    determine one or more forces between the one or more ligands and the specific receptor based upon the alchemical free energy of the system;
    provide the one or more forces to the molecular dynamics engine to accelerate the speed of the structural change of the one or more ligands to overcome one or more free energy barriers in the orthogonal space;
    generate a first file storing time-dependent free energy parameter changes associated with the alchemical free energy of the system;
    generate a second file storing current data associated with the alchemical free energy of the system;
    generate a third file storing time-dependent energy values associated with the alchemical free energy of the system; and
    generate a fourth file storing orthogonal space free energy surface data associated with the alchemical free energy of the system;
the molecular dynamics engine configured to;
    predict, based on at least one of the first file, the second file, the third file, and the fourth file, one or more chemical state related thermodynamic properties of the system based upon the determined alchemical free energy of the system; and
    identify one or more potentially therapeutic drug candidates by identifying one or more ligands that are most likely to bind strongly to the specific receptor based upon the predicted one or more chemical state related thermodynamic properties of the system.

6. The apparatus according to claim 5, further comprising an input generator configured to provide one or more inputs, including a molecular structure and the modified energy function to the OST engine and the molecular dynamics engine.

7. The apparatus according to claim 5, wherein the OST engine is further configured to provide one or more outputs including a molecular trajectory and the alchemical free energy of the system.

8. The apparatus according to claim 5, wherein the OST engine is further configured to perform double-integration recursion.

9. The apparatus according to claim 8, wherein the double integration recursion is based on dynamic reference restraining.

10. A non-transitory computer readable medium containing program instructions for identifying method one or more potentially therapeutic drug candidates by simulating systems of molecules through molecular dynamics, the method comprising:
    initializing a molecular dynamics engine in a first CPU or GPU;
    initializing an orthogonal space tempering (OST) engine in a second CPU or GPU, wherein the first CPU or GPU is independent of the second CPU or GPU;
    at each of a plurality of propagation steps of the molecular dynamics engine;
    determining, by the orthogonal space tempering (OST) engine, an alchemical free energy of a system comprising one or more ligands and a specific receptor in an orthogonal space by performing orthogonal space tempering utilizing a second-order generalized ensemble, wherein the second-order generalized ensemble is a generalized orthogonal space random walk (OSRW) method having an effective sampling boundary imposed by a pre-selected orthogonal space sampling temperature ($T_{ES}$) and described by a modified energy function as $$U_m = U_o(\lambda) + f_m(\lambda) + \frac{T_{ES}-T_0}{T_{ES}} g_m(\lambda, F_\lambda)$$

where $\lambda$ is an alchemical order parameter, $U_O(\lambda)$ stands for a hybrid energy function that is constructed on the basis of the constraints of $U_0(0)=U^A$ and $U_1(0)=U^B$, wherein two ends states A and B respectively represented by $\lambda=1$ and $\lambda=0$, $f_m(\lambda)$ is adaptively updated to approach $-G_0(\lambda)$, $g_m(\lambda,F_\lambda)$ is adaptively updated to approach $-G_0(\lambda, F_\lambda)$ and the contribution of $g_m(\lambda,F_\lambda)$ is scaled by a parameter $$\frac{(T_{ES}-T_0)}{T_{ES}},$$

wherein $T_0$ is a system reservoir temperature and $T_{ES}$ is a present parameter referred to as the orthogonal space sampling temperature;
    determining, by the orthogonal space tempering (OST) engine one or more forces between the one or more ligands and the specific receptor based upon the alchemical free energy of the system;
    providing the one or more forces to the molecular dynamics engine to accelerate the speed of the structural change of the one or more ligands to overcome one or more free energy barriers in the orthogonal space;
    generating, by the OST engine, a first file storing time-dependent free energy parameter changes associated with the alchemical free energy of the system;
    generating, by the OST engine, a second file storing current data associated with the alchemical free energy of the system;
    generating, by the OST engine, a third file storing time-dependent energy values associated with the alchemical free energy of the system;
    generating, by the OST engine, a fourth file storing orthogonal space free energy surface data associated with the alchemical free energy of the system;
    predicting, based on at least one of the first file, the second file, the third file, and the fourth file, one or more chemical state related thermodynamic properties of the system based upon the determined alchemical free energy of the system; and
    identifying one or more potentially therapeutic drug candidates by identifying one or more ligands that are most likely to bind strongly to the specific receptor based upon the predicted one or more chemical state related thermodynamic properties of the system.

11. The non-transitory computer readable medium according to claim 10, further comprising instructions for initializing the OST engine and the molecular dynamic engine using one or more inputs, including a molecular structure and an energy function.

12. The non-transitory computer readable medium according to claim 10, further comprising instructions for providing one or more outputs, including a molecular trajectory and the alchemical free energy of the system.

13. The non-transitory computer readable medium according to claim 10, wherein performing orthogonal space tempering further comprises, performing double integration recursion.

14. The non-transitory computer readable medium according to claim 13, wherein the double integration recursion is based on dynamic reference restraining.

* * * * *